(12) United States Patent
Iwig et al.

(10) Patent No.: US 7,607,256 B2
(45) Date of Patent: Oct. 27, 2009

(54) POROUS, LIGHT TRANSMISSIVE MATERIAL AND METHOD FOR USING SAME

(75) Inventors: Mark M. Iwig, Johnston, IA (US); Mitchell Brett Callaway, Baxter, IA (US); Daniel M. Goldman, Des Moines, IA (US); Kirby L. Kester, Kalaheo, HI (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 114 days.

(21) Appl. No.: 11/021,435

(22) Filed: Dec. 22, 2004

(65) Prior Publication Data

US 2005/0229483 A1  Oct. 20, 2005

Related U.S. Application Data

(60) Provisional application No. 60/624,790, filed on Nov. 3, 2004, provisional application No. 60/532,018, filed on Dec. 22, 2003.

(51) Int. Cl.
*A01H 1/02* (2006.01)
(52) U.S. Cl. ......................................................... 47/1.41
(58) Field of Classification Search ................... 47/1.41, 47/58.1 FV
See application file for complete search history.

(56) References Cited

U.S. PATENT DOCUMENTS

| | | | |
|---|---|---|---|
| 1,820,040 A | | 8/1931 | Zuckerman |
| 2,056,514 A | * | 10/1936 | Anselmo ........................ 47/32 |
| 2,446,509 A | * | 8/1948 | Fischer ........................ 47/29.1 |
| 3,111,799 A | * | 11/1963 | Schmit et. al. .................... 56/1 |
| 3,727,345 A | | 4/1973 | Smith |

(Continued)

FOREIGN PATENT DOCUMENTS

EP  1 174 512 A1  1/2002

(Continued)

OTHER PUBLICATIONS

Hume, A.N., "A Possible New Method for the Control of Pollination of Corn", J. Am. Soc. Agron., vol. 33, No. 3, Mar. 3, 1941, p. 265-266.*

(Continued)

*Primary Examiner*—Francis T Palo
(74) *Attorney, Agent, or Firm*—McKee, Voorhees & Sease, P.L.C.

(57) ABSTRACT

An apparatus and method to isolate at least a part of a plant from passage of things or materials of certain size or characteristics. In one aspect, a shroud or sock (10) of material can be removably placed over at least a part of the plant (3) with a releasable closure (13). The material is highly permeable to air and moisture and is substantially light transmissive. However, it has a pore size which blocks the undesirable materials or things (e.g., pollen or insects). The material can have a relatively light weight so that it can be optionally suspended by the plant (3) without significant effect on the growth or health of the plant. The material can have substantial tensile strength to resist deformation, tearing, or puncture during normal handling or in moderate to high winds. It can be utilized to provide a barrier over a part of a plant, substantially an entire plant, or a plurality of plants.

34 Claims, 6 Drawing Sheets

U.S. PATENT DOCUMENTS

| | | | |
|---|---|---|---|
| 4,159,596 A | 7/1979 | Downing | |
| 4,291,082 A | 9/1981 | Stall | |
| 4,304,068 A | 12/1981 | Beder | |
| 4,554,761 A | 11/1985 | Tell | |
| 5,689,914 A | 11/1997 | Greaves | |
| 6,141,904 A | 11/2000 | Greaves | |
| 6,282,835 B1 | 9/2001 | Richtsmeier | |
| 2004/0132370 A1 | 7/2004 | Schroder | |
| 2005/0229483 A1* | 10/2005 | Iwig et al. | 47/58.1 R |

FOREIGN PATENT DOCUMENTS

| | | | |
|---|---|---|---|
| FR | 2 638 059 A1 | 10/1988 | |
| FR | 2159268 | 4/1990 | |
| FR | 2638059 A1 * | 4/1990 | |

OTHER PUBLICATIONS

"Self Pollination Auto Fecondation", Sales page, OSMOLUX: Emerging Technologies—No Contamination, No Rotting-, pantek-france@wanadoo.fr.

Hume, A.N., "A possible new method for the control of pollen in corn", J. Am. Soc. Agron. vol. 33, No. 3, Mar. 1941, p. 265-266.

Stern, R. "Tunnels Go Supersize", The Grower, Jun. 2007 (3 pages).

* cited by examiner

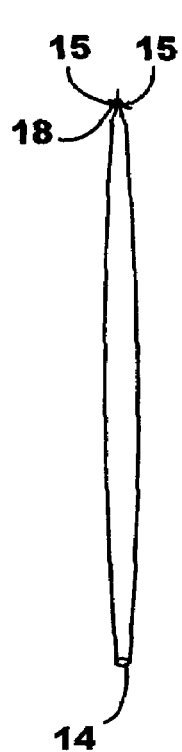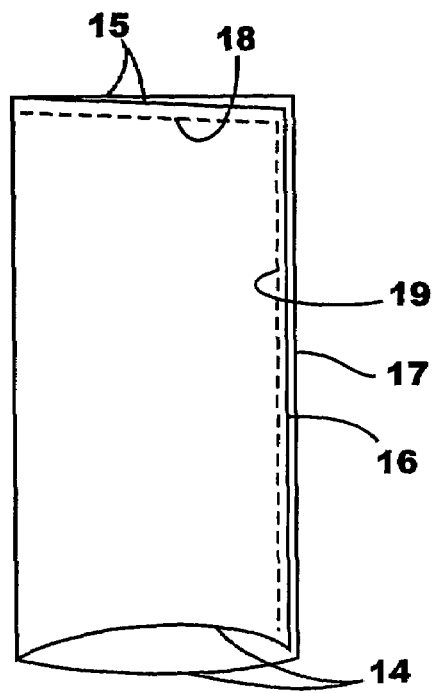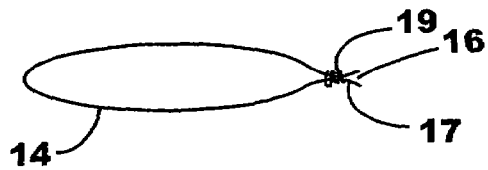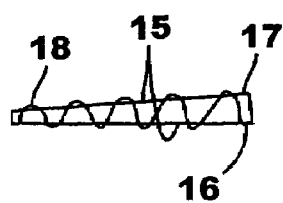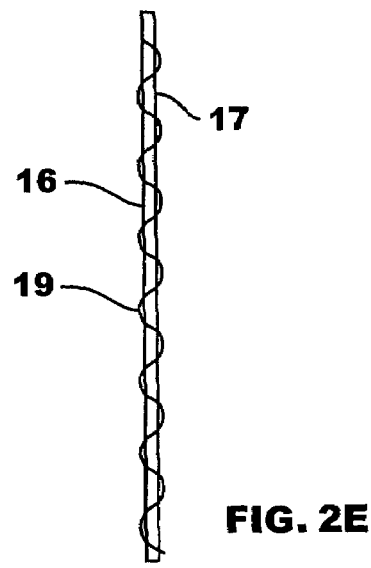
FIG. 2G
FIG. 2C
FIG. 2F
FIG. 2D
FIG. 2E

POROUS, LIGHT TRANSMISSIVE MATERIAL AND METHOD FOR USING SAME

REFERENCE TO RELATED APPLICATIONS

This is a conversion of and priority to the following applications is made under 35 U.S.C. Sections 119(e) and/or 120: Ser. No. 60/624,790 filed Nov. 3, 2004 and Ser. No. 60/532,018, filed Dec. 22, 2003.

INCORPORATION BY REFERENCE

The contents of U.S. Ser. No. 60/624,790 filed Nov. 3, 2004, U.S. Ser. No. 60/587,240, filed Jul. 12, 2004, and U.S. Ser. No. 60/532,018, filed Dec. 22, 2003, are incorporated by reference herein in their entireties.

BACKGROUND OF THE INVENTION

A. Field of the Invention

The present invention relates to an apparatus and method for a barrier system which allows the selective shielding of plants from certain things; and in particular, to a barrier which passes a desired amount of plant growth requisites while blocking undesired substances from the plants. In one aspect of the invention, the barrier is used in pollination breeding experiments to control or block pollen without detrimental effect on growth of the plant or seed yield or other undesirable results.

B. Problems in the Art

The development of plant breeding has occurred for many years. The basic concept involves selecting a plant to breed with another plant to produce an offspring with improved or desired characteristics. To be effective, the cross-pollination must be accurate. Desired pollen from the male part of one plant must be collected and emplaced on the female part of the second plant at the proper time without contamination by undesirable pollen. Presently, conventional cross-pollination methodology requires multiple passes through the experimental plot. The first pass looks for female shoots. A worker covers each female shoot, typically with a small sack, to protect it against receiving undesirable pollen. If not covered, it would be exposed to anything. Undesired pollen could be carried by wind, insects, birds, or workers and contaminate the female shoots.

The second pass puts small covers over the male parts of the plants to collect the pollen they generate.

On another pass selected female shoots are pollinated with desired pollen, which requires removing the covers from the male parts of a first plant, carrying the pollen to the female part of the second plant, and physically depositing the same.

This typical cross-pollination process is labor intensive. In requires multiple field passes, coverings, uncoverings and collection. Conventionally, it concentrates on individual parts of individual plants, e.g., small-sized single sacks for small parts of individual plants. The process covers only the part of the plant at risk, uses less material that way, and has lower risk of stunting or otherwise effecting normal growth of the plant because only small, non-leaf parts are covered, and only for a limited amount of time.

However, the magnitude of required labor resources is substantial. It is very labor intensive. Typically, larger seed companies may have on the order of millions of pollinations per year. Therefore, there is room for improvement in the art with respect to the expenditure of human resources. Also, whatever system is employed must be cost effective.

Other issues exist. For example, the quality of pollination must be very high. This raises human error issues for such a labor-intensive task. While wind is a major cause of pollen load in the air, the movement of so many persons through experimental plots increases the risk of contamination by jarring and loosening pollen or carrying pollen in from other plots. Pollen load in the air is increased with movement of people through fields, adding and removing sacks to parts of plants, and not being able to cover all male parts of plants instantaneously. Pollen load increases the risk of contamination.

There are other perhaps more subtle issues. Any foreign addition to a plant may adversely effect its normal growth and development. Even small sacks over female and male parts may diminish the amount of air and moisture to that part of the plant or constraint growth. Also, severe or bad weather may degrade development.

The significant amount of labor involved in artificial pollination creates safety issues. Repetitive stress injury, transportation, long hours and tedium are often side effects of this type of work. This can result in physical injury or accuracy problems.

Low-level contamination is difficult to detect. However, the advent of genetically modified organism (GMO) crops has greatly increased the need to minimize or eliminate contamination.

Therefore, there is need for improvement in the art over typical, historical cross-pollination and insert pollination breeding methods, particularly in light of an increasing number of factors and regulations at play. There is also room for improvement in selfing experiments. It would be advantageous to decrease labor overhead. It would also be advantageous to provide a better barrier between plant and external environment for selected blockage of things. Ideally, control or blockage of all pollen would be desirable.

Various barricades or covers for more than just parts of plants have been tried. For example, cheese-cloth type fabrics have been placed over seedling beds of tobacco plants to shield them from insects and direct sunlight but allow air and water to pass sufficiently so that they can grow to the stage where they could be transplanted to the fields. Another example is canola, which is particularly susceptible to bees carrying in contaminating pollen.

Based on knowledge and belief, these attempts are either limited to use of fabric for a short period of time and for a basic shading function, such as the tobacco seedlings, or to a barrier against insects, but not pollen particles themselves. In both examples, sufficient air and water must pass through the covers to sustain and not detrimentally affect the plants. This, using these conventional materials would require pore sizes larger than most pollen particles.

In some cases where temporary covers are used, the permeability to air, water and light is not high. Sustained covering of the plant could result in adverse effect on growth of the plant or even sustenance of the plant. Also, lack of or reduced breathability or air flow could create super-heated conditions that could burn or stunt the plants. Some covers intentionally thermally insulate a plant. They tend to limit air flow or exchange and have insulating material which increases size and reduces flexibility of the device. They may require some structure to make them self-supporting, and thus, many times have somewhat rigid elements.

There is presently no known adequate solution to these issues.

SUMMARY OF THE INVENTION

It is therefore a principle object, feature, aspect and/or advantage of the present invention to provide an apparatus and method which solves or improves over the problems and deficiencies in the art.

Further objects, features, aspects and/or advantages of the present invention include an apparatus and method for a barrier for plants which:

a. enable better control of plant breeding experiments;
b. improves the quality and/or provides higher success rate of pollination in pollination processes or at least provides results as good as traditional methods;
c. is less labor intensive for plant breeding experiments;
d. does not substantially negatively effect normal health of plants;
e. can block pollen without compromising health of plants;
f. isolates plants from many undesirable things external of the plant, other than air, moisture and light;
g. improves flexibility of plant breeding experiments, including providing a more flexible window of time for completing pollinations for a group of plants;
h. minimizes potential for foreign pollen contamination;
i. can reduce the use of pesticides, fungicides and herbicides;
j. is relatively economical;
k. is durable;
l. promotes better efficiency in plant breeding.

The present invention includes an apparatus and method for providing, for a plant part, a plant, or a plurality of plants, a barrier to pollen while allowing desirable light and air exchange. In one aspect of the invention, the barrier comprises a thin, lightweight, air and water permeable, light transmissive material configured into a covering for at least a substantial part of a plant, or a plurality of plants, where the material can be draped on and around the plant, and supported by the plant, or supported by super structure. In the context of plant breeding, the material can be adapted to block substantially all pollen relevant to the type of plant without material inhibition, disruption, or affect on normal plant growth. In another aspect, the material can retain pollen from a plant or set of plants inside a shroud or tent.

In on aspect of the invention, an apparatus comprises a barrier to selected materials that can be placed over a part of or substantially a whole plant or a plurality of plants. The barrier has relatively high permeability to air and moisture but relatively small pore size. It is substantially light transmissive. It is relatively lightweight. It has a tensile strength that is resistant to deformation, tearing or puncture through normal handling or presence of moderate to high winds. It includes a structure or mechanism to install or remove it from a plant.

In another aspect of the invention, a barrier comprises a material dedicated to prevent passage of external pollen, but has sufficient permeability and transmissivity to allow passage of air, moisture and light so that there is not a significant inhibition, disruption or affect on normal plant growth. The material is flexible enough to be placed over and substantially encapsulate at least a part of a plant.

In another aspect of the invention, a barricade comprises a relatively small pore size material in the form of a sock or sack adapted to be placed over at least a part of a plant. The properties of the material include relatively lightweight, substantially air and water permeable, with a substantial amount of light transmissivity. A releasable closure at or near an opening to the sock or sack allows it to be cinched around a portion of the plant to substantially encapsulate at least a portion of the plant.

A still further aspect of the invention comprises a barricade to corn pollen and insects. The barricade is substantially a lightweight, flexible, air and moisture permeable, and light transmissive material formed into a sock or sack with a releasable closure for substantially encapsulating at least a part of a corn plant.

A further aspect of the invention comprises a method for isolating a least a part of a plant from undesirable things, including insects and pollen, by shrouding at least a part of the plant with a material that is substantially air and moisture permeable, light transmissive, lightweight, and resistant to deformation, tearing, or puncture by normal handling or moderate to high winds.

A still further aspect of the invention is an apparatus and method for isolating a plurality of plants from selected things by essentially encapsulating the plurality of plants with a material that is substantially permeable to air and moisture, light transmissive, relatively lightweight, and resistant to deformation, tearing, or puncture by normal handling or moderate to high winds, while at the same time blocking undesirable things including pollen of certain types and insects.

These and other objects, features, aspects and/or advantages of the present invention will become more apparent with reference to the accompanying specification, including the drawings.

BRIEF DESCRIPTION OF THE DRAWINGS

FIGS. 2A-G are illustrations of fabrication of the embodiment of FIG. 1.

DETAILED DESCRIPTION OF EXEMPLARY EMBODIMENTS

A. Overview

Figure 1:
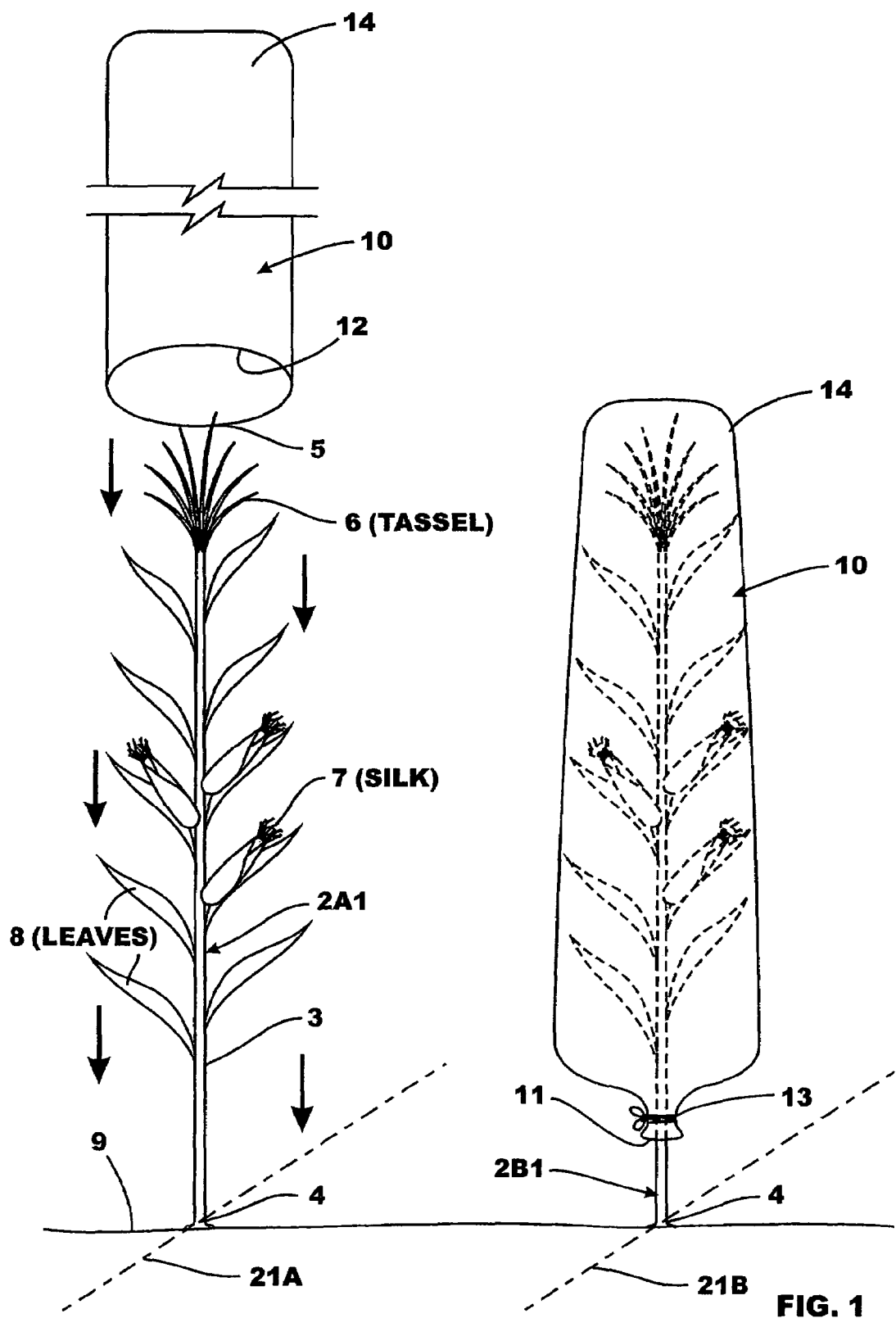
FIG. 1 is a perspective view of one exemplary embodiment of the present invention applied to single corn plants.

The present invention can take many forms and embodiments. For a better understanding of the invention, specific exemplary embodiments will now be described in detail.

Reference will be made at times to the appended drawings. Reference numerals and letters will be used to indicate certain parts and locations in the drawings. The same reference numerals or letters will be used to indicate the same parts and locations throughout the drawings unless otherwise indicated.

B. General Environment of Exemplary Embodiments

Each of the exemplary embodiments will be described in the context of utilization with corn plants in a corn breeding work using pollination. This includes, but is not limited to, breeding, production or other functions. Most of the principles regarding the invention will also apply to other types of plants, and the invention is not limited to corn.

Furthermore, as previously indicated, principles of the invention are not necessarily limited to plant breeding experiments.

C. Exemplary Embodiment Example 1

What will be called plant sock 10 (FIG. 1) is made of a flexible, semi-permeable material elongated between an open end 12 and a closed end 14. Plant sock 10 defines an enclosed space with one opening 12 and is adapted dimensionally to slip over top 5 of a developing corn plant 2, slide down without damage or detriment over the tassel or male part 6, female parts 7, and leaves 8 of plant 2 towards the bottom 4 of plant 2, and be supported by plant 2.

As shown in FIG. 1 regarding the left-hand plant (indicated as plant 2A1), opening 12 must be wide enough to pass all the way by the foliage and reproductive parts 6, 7, 8 of plant 2A1. The low weight of sock 10 is such that it would gently lay on and be supported by plant 2 once in position (right-most sock 10 on plant 2B1 in FIG. 1). Sock 10 is pre-designed to have a shape that generally follows the shape of a corn plant; however, extra space is built into sock 10 to allow for normal plant growth over the normal amount of time sock 10 would be deployed on the plant. For example, an extra 8 to 10 inches of room at the top of sock 10 should allow for tassel growth without breaking or material damage. The tassel may bend a bit, but the extra space and light weight of sock 10 should not be materially detrimental to it.

A tie 13 or other removable fastener could be used to bind the bottom of sock 10 to or around stem 3 of plant 2 (e.g. below the lowest ear of plant 2). Alternatively, a rubber band, drawstring, or elastic cuff could be used. They could be separate from sock 10 or incorporated into sock 10. Some examples of material for sock 10 for corn are listed in Table A below. Such materials can have the following properties and characteristics:

a. Permeability. The material is relatively highly permeable to air and moisture, but has relatively small pore sizes such that most, if not all, corn pollen likely will be blocked from passing through. Thus, most, if not all, insects would likewise be blocked. It is preferable that the material be breathable even in wet environments. As can be appreciated, pollen can vary in size. Corn pollen tends to be on the order of 80 to 100 µm in diameter. Therefore, it is preferable that the material block these sizes and have pore sizes below that range, e.g. in the range of 60-80 µm, to block corn pollen but maximize permeability for air exchange. However, as stated, corn pollen has size variability. Also, forces such as wind and rain can drive pollen into the material, even if pore size is smaller than the pollen. Therefore, one suggested range of pore sizes for the material is to have pore sizes of no greater than the mid 60's, and perhaps even the low 60's. Therefore, one suggested range of pore sizes for the material is approximately 60-80 µm. It may be preferable to use material with mean or average pore size of 75 µm or less. For some materials a range of 60-70 µm is preferred. It is to be understood that other sizes may be desirable for different goals or for different types of plants. A Frazier value on the order of 650-1000 $ft^3/ft^2$/min. or higher is believed preferable.

b. Light transmissivity. Light transmissivity is high. Most light, including sunlight, would pass through. Opacity is around 46%. A PAR transmissivity value of at least 50% (at least for 500 to 730 nm wavelength light) is believed preferred. Light quality is similar to ambient.

c. Weight. Weight is relatively light (e.g. on the order of less than one ounce per square yard). It is preferable that the material be light enough to gently drape over the plant and not weigh down the foliage. It should have enough volume to allow the plant to grow.

d. Strength. Tensile strength is sufficient to resist deformation, tearing, or puncture through normal handling or in the presence of moderate to high winds. This factor varies for different materials. One example is a material with tensile MD/XD of 10.3/4.2 lb/in. and tear MD/XD of 1.4/1.5 lb. It can be UV light resistant if desired. While strength sufficient to withstand tearing or ripping in wind or during handling is preferable, it is desirable that it be durable, washable, and non-abrasive (at least on the interior). Additional support can be added. For example one or more additional layer(s) of material can be added as support layer(s). The support layer (s) can have much larger openings and function to provide necessary strength for the layer having the properties described above.

Other characteristics and properties are available from the manufacturer.

Cost of the material may be a factor. It many times could be desirable to minimize cost. The range of current prices per square yard of materials such as listed in Table A can vary substantially (e.g. from around $0.10 to $60.00/$yd^2$). Therefore, if cost is a factor, a lower cost material might be selected. However, there may be trade-offs between price and performance.

In a corn breeding experiment, plant sock 10 basically presents a barricade or pollen filter to all external corn pollen to isolate an entire plant 2 from natural pollination for a desired period during the growing season. At the same time, it does not materially alter the natural growing conditions of the plant, allowing good air and moisture transfer, as well as sunlight to the plant. It does not burden the plant by its weight and resists buildup of heat because of its breathability.

It is relatively quick and easy to place over a plant or remove. One simply slips sock 10 over plant 2 and uses a releasable closure at the bottom (e.g. drawstring, an elastic cuff, or even a metal binder clamp of the type used to hold multiple sheets of paper together). A lace, rubber band or other closure or binder could be used. The sock may only extend down to, or might be bound to the plant, just below its reproductive parts, instead of substantially to the bottom of the plant. The lower foliage act as a mechanical stop to restrain sock 10 from sliding up the plant, even in relatively high wind or if pulled upward. The sock-like structure preferably deflects, absorbs, or otherwise handles even relatively high wind without great risk of ripping or tearing.

The size of sock 10 is selected to allow plant 2 to grow substantially in height and width without constraint. It is generally better to be "baggy" around the plant than closely fitting.

Figure 2A:
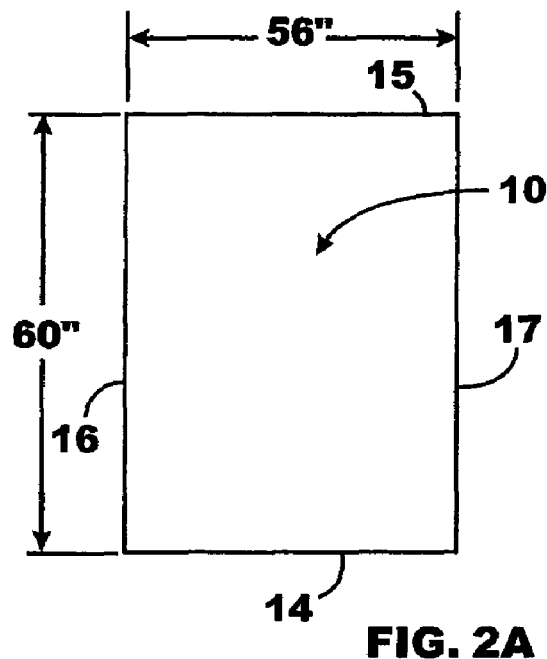
Figure 2B:
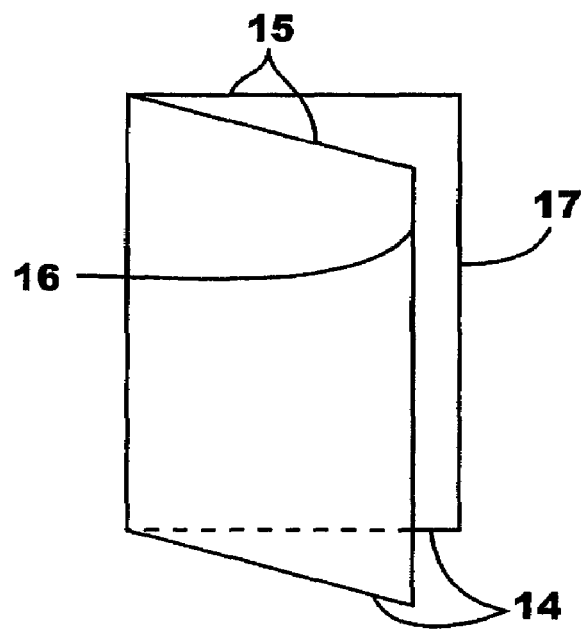

FIGS. 2A-G illustrate one method of fabricating plant sock 10. A 56 inch wide by 60 inch long sheet of material is produced or cut out (FIG. 2A) having what will be called here, for convenience, bottom edge 14, top edge 15, left edge 16, and right edge 17. The sheet is folded in half lengthwise (FIG. 2B). Adjacent portions of top edge 15 can be stitched together (and/or sealed with a bonded seam) (diagrammatically indicated at reference number 18), as can adjacent portions of edges 16 and 17 (stitches 19) (see FIG. 2C). FIGS. 2D-F diagrammatically indicate top, opposite side and bottom views respectively of the assembled plant sock 10. The edges are stitched-together edges with strong, durable (even in sunlight and outside conditions) thread in a manner which basically seals those sides of sock 10. FIGS. 2A-F merely diagrammatically illustrate manufacturing steps for a sock 10. They are not to scale or precise illustrations.

Although FIGS. 2A-G illustrate a bag or sock that is basically rectangular, it may be advantageous for it to be tapered, such as indicated in the right-hand side of FIG. 1. For example, a sock that is around 60 inches tall might 9 inches wide at the top but taper out to around 28 to 32 inches at the bottom. This can make it easier to install and it would more closely follow the shape of a grown corn plant. The leaves could better help support the bag along the whole plant, rather than just in a few locations.

If stitches are used needle size, stitch density, and thread type should be selected to prevent any opening likely to allow passage of pollen that the material of the sock is designed to exclude. One example for this embodiment would be standard bonded polyester thread (e.g. tex 92 at 6-8 stitches per inch) for the seams. A cotton liner could be used to fill needle hole areas. Alternatively, bonded seams could be used (ultrasonic or adhesive bonding) with heat or weld seal so long as it would not materially weaken the fabric.

D. Second Exemplary Embodiment

Figure 3:
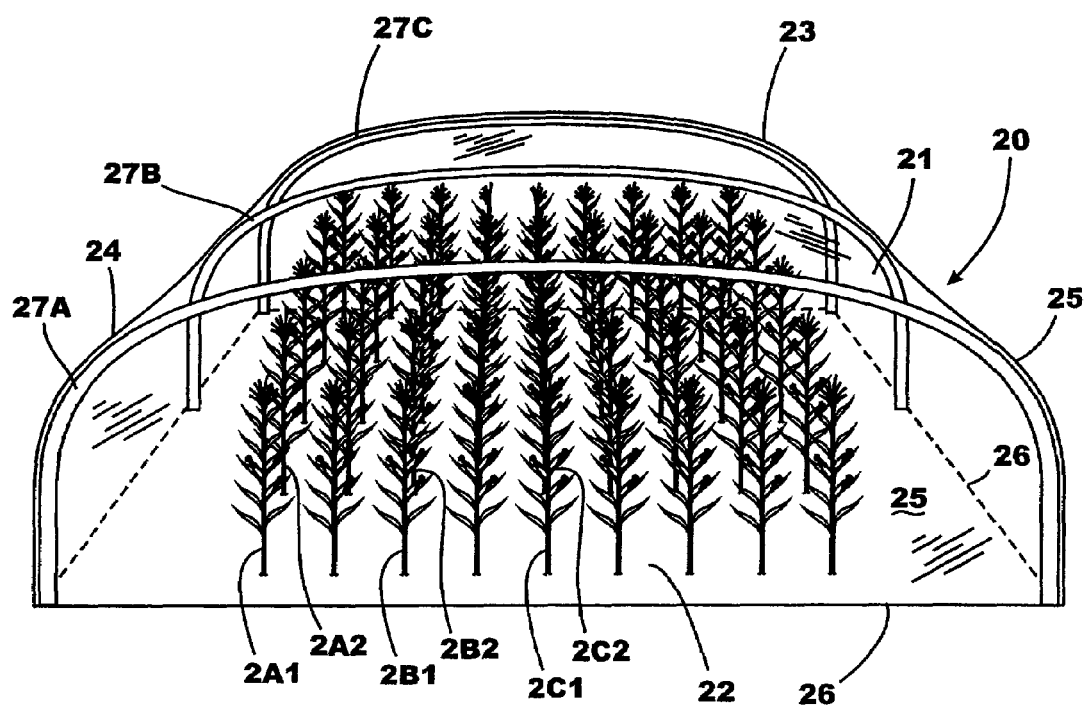
FIG. 3 is a perspective view of another exemplary embodiment of the present invention applied to a plurality of corn plants.

FIG. 3 illustrates a super-structure or framework 27 from which a shroud or barrier 20 can be suspended to simultaneously cover a plurality of plants 2. In FIG. 3, the super-structure is a plurality of arches 27A, B and C spaced apart and generally parallel, having lower portions anchored in the ground (e.g. direct-buried or in some type of subsurface footing). A sheet or shroud 20 of material having similar properties to plant sock 10 is draped over framework 27 to enclose the plants. The rectangular pyramid shape of material 20 has an open bottom, top 21, front 22, back 23, left side 24, and right side 25. The lower edges of sidewalls 22, 23, 24, 25 extend down to the ground to completely enclose the plurality of plants 2 inside.

Instead of encapsulating substantially all of, and being supported by a single plant, shroud 20 substantially encapsulates one, two or more plants but is supported by an independent super-structure. Stakes or other ground securing methods can be used to hold the lower edges of the shroud to the ground to provide a barrier against airborne pollen or insects for plants 2.

Frame members 27 can be made of relatively inexpensive light-weight materials, such as relatively light-weight tubular metal or plastic (e.g. PVC), because of the relatively light weight of the material of shroud 20. Supports 27 could be similar to those used to suspend batting cage nets. The height, width and depth of shroud 20 can be designed to have all portions of shroud 20 spaced apart from any part of the plants to be enclosed therein. Depending on desire and need, the walls of shroud 20 could be close to the plants, to conserve material and space, or substantially spaced from any part of any plant to allow for plant growth, machines, or head room for workers.

Shroud 20 could be in the form of a rectangular prism, with generally planar sides and top when erected. It could be made out of several independent sheets of the material sewed or otherwise connected together to form an integral unit. Other shapes are possible, e.g. hemispherical, a rotated portion of an ellipse or parabola, pyramidic, etc., or combinations thereof. It could have irregular shape. The supports could be external or internal, or both.

Workers could enter the interior of the shroud by lifting up a bottom edge of a sidewall. Alternatively a slit in one side wall could be normally held together but openable for entrance.

E. Third Exemplary Embodiment

Figure 4:
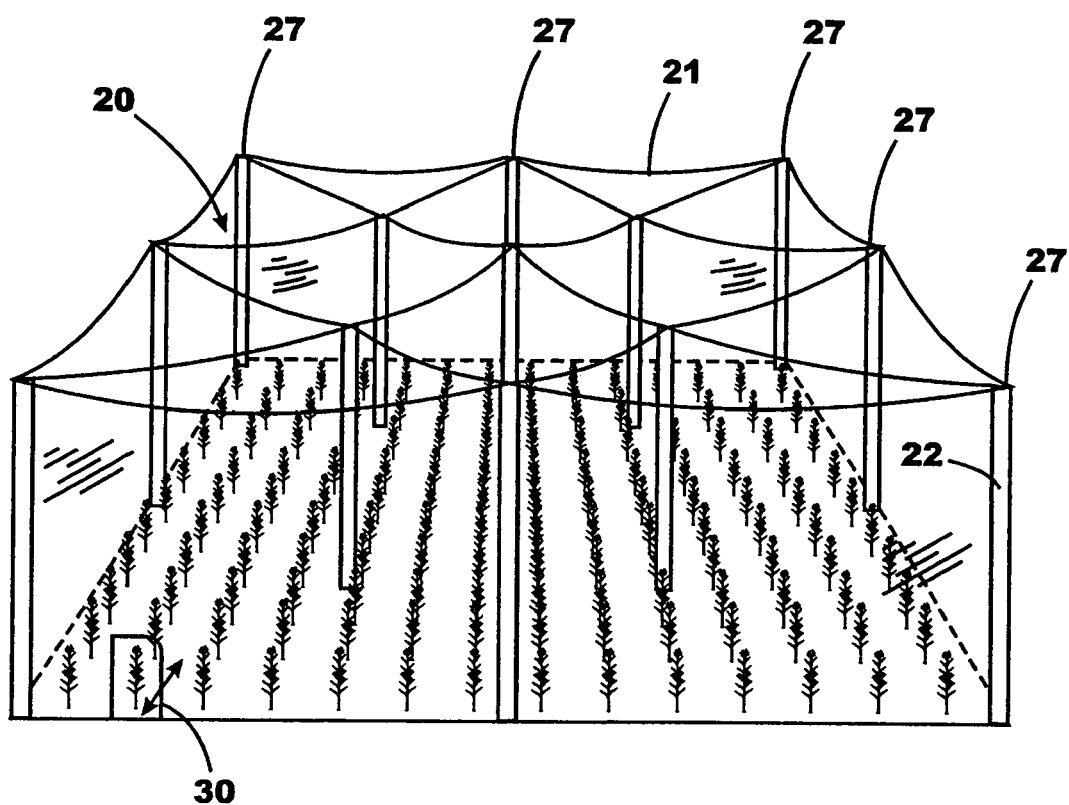
FIG. 4 is an additional exemplary embodiment of the present invention applied to a field or experimental plot of plants.

FIG. 4 illustrates a shroud or barrier 20 of material similar to that of plant sock 10 except on an even larger scale than shroud or barrier 20 of FIG. 3. Substantially tall poles 27 (e.g. 15-100 feet) could be distributed across a substantial area (e.g. an experimental plot, a field, or a portion of a field). Material 20 could be suspended over poles 27 above the plants with the bottom edges of shroud 20 extending to the ground. In this example, a plurality of rows of plants is shown enclosed under shroud or barrier 20. A first row of plants A is enclosed, as are additional rows B, C, . . . , N.

In conventional experimental breeding programs for corn, experimental plots of a few rows wide by several tens of feet or yards long could each be enclosed by a shroud 20 to isolate that set of plants from pollen and insects, and to present a barrier between the plants and the exterior, above-ground environment, without materially effecting passage of those things needed to sustain normal growth of the plants. It could be larger.

The interior of tent or shroud 20 shown in FIG. 4 could, if desired, be subdivided by similar material. In other words, row A could be isolated from row B by a vertical sheet of material between the rows from top of the interior of the shroud to the ground. Other rows, or portions of rows, could likewise be separated.

F. Fourth Exemplary Embodiment

Figure 5:
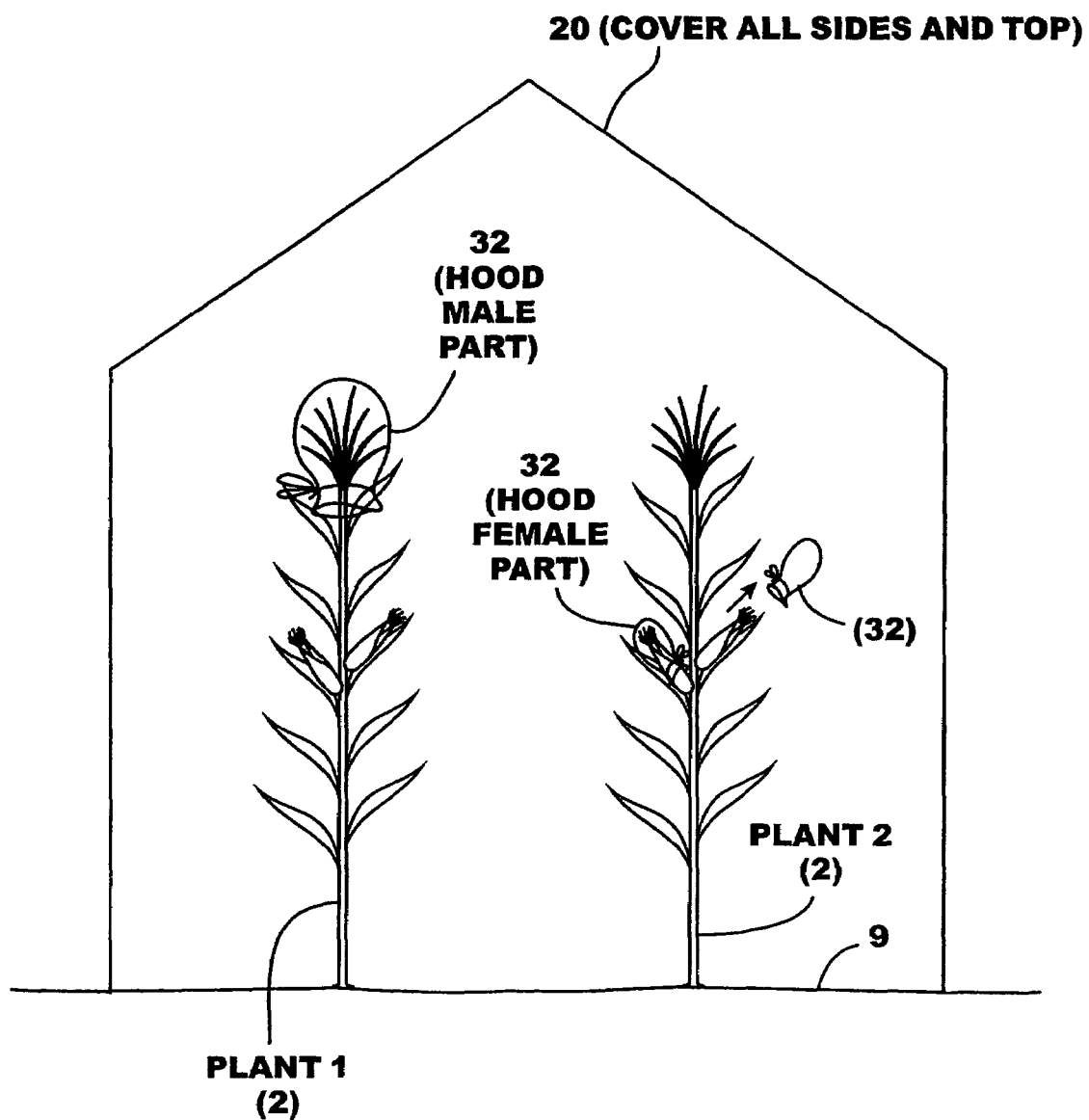
FIG. 5 is an elevation diagrammatic depiction of another exemplary embodiment of the present invention utilizing a covering for a plurality of plants and smaller coverings for parts of individual plants.

FIG. 5 illustrates diagrammatically a tent or shroud 20 positioned over one or more plants 2, enclosed on all sides and top with a material similar to that of plant sock 10 of FIG. 1. Small socks 32 (also made of similar material) could be selectively positioned over a part or parts of a single plant, but not the whole plant. For example, the male parts of both plants 1 and 2 could be socked or enclosed while each the female part of plant 2 is socked or enclosed, while both plants are tented or enclosed by an overriding cover 20. At the appropriate time, the tassel or male part of plant 2 could be unsocked, leaving all female parts of plant 2 socked, to encourage pollination of plant 1 by plant 2, and deterring self-pollination. With multiple sets of plants 1 and 2, this might be useful in prohibiting pollination between plants from the same population, using cross-pollination with pollen from plants from another population. As can be appreciated, instead of smaller socks 32, whole plant socks 10 could be used for certain functions under a tent 20.

Also a sock 32 could be placed over both male and female parts of the same plant. Shroud 20 could act simply as a barrier to other pollen or insects. Or, selective placement and removal of socks 32 on the same plant could encourage self-pollination.

Alternatively, entire plant socks such as plant socks 10 in FIG. 1 could be placed over selected plants within a larger shroud 20. Selective use of socks 32 on tassels could reduce pollen load in the air.

G. Options and Alternatives

It can therefore be seen, through illustrations and each of the exemplary embodiments, that the present invention, in its various aspects and embodiments, provide an advantageous barrier. In the case of corn and a corn breeding experiment, one embodiment of the material of the sock, shroud or tent would preferably block most if not all corn pollen, based on selection of pore size that is at least less than the typical range of diameters of corn pollen particles. Such relatively small pore size would block most insects. But, at the same time, the properties of the material include high transmissivity of light and high permeability of air and moisture so that these primary, essential components for plant growth are not materially attenuated.

It is to be understood, however, that the invention can take many forms and embodiments. The exemplary embodiments given herein are for illustration purposes only and not by limitation. Variations obvious to those skilled in the art will be included within the invention.

For example, the precise dimensions and shape of a sock, shroud, or tent according to the present invention, can vary as desired or needed.

Likewise, the material itself can vary somewhat according to desire or need. Table A below sets forth a plurality of examples of materials which appear to have properties which would work with aspects of the present invention relative to corn pollen. Some are woven, some are non-woven. Non-woven materials tend to be less expensive than woven materials, which could be a significant advantage.

Still others from Safer Nitex (Kansas City, Mo. USA) include:

Nitex 64/47 ((average pore size (in μm)/% effective open area)

Nitex 64/45

Nitex 70/49

The materials in Table A, and the other examples have the following relatively consistent characteristics:

a. weight of material;

TABLE A

| Substrate | Type | Technology | BW oz/yd2 | Thickness (mil) | Tensile MD/XD (lb/in) | Tear MD/XD (lb) | Frazier ft3/ft2/min | MVTR | Minimum Pore Size | Mean Pore Size | Maximum Pore Size | Opacity | Slip Angle MD/CD | COF MD/CD |
|---|---|---|---|---|---|---|---|---|---|---|---|---|---|---|
| Woven | 73 micron PET | Woven PET | 1.0 | 2.1 | 29.3/26.4 | 0.6/0.6 | 979.5 | 2035.5 | 48.1 | 77.6 | 84.1 | 26.8 | 52/48 | 0.6/0.8 |
| Woven | 59 micron PET | Woven PET | 1.1 | 2.0 | 31.5/30.9 | 0.6/0.6 | 744.5 | 1979.2 | 40.6 | 55.0 | 56.4 | 29.1 | 48/49 | 0.7/0.7 |
| Woven | NMO 75 micron | Woven Nylon | 1.1 | 2.5 | 34.7/39.8 | 0.9/1.0 | 888.0 | 2030.7 | 53.3 | 75.0 | 85.2 | 24.4 | 53/50 | 0.8/0.7 |
| Woven | NMO 55 micron | Woven Nylon | 1.0 | 2.3 | 33.4/33.4 | 0.8/0.80 | 688.8 | 1959.7 | 30.2 | 58.1 | 62.1 | 26.2 | 54/45 | 1.0/0.7 |
| ACT | | Spunbond PET/PE | 1.0 | 5.3 | 10.2/4.8 | 1.5/2.0 | 416.2 | 2080.9 | 26.8 | 67.7 | 134.1 | 30.6 | 74/65 | 3.8/3.6 |
| ACT | | Spunbond PET/PE | 1.8 | 9.5 | 22.7/13.6 | 2.3/3.7 | 184.5 | 2011.3 | 17.6 | 44.1 | 75.9 | 57.1 | 77/77 | 3.8/3.8 |
| ACT | Blue color | Spunbond PET/PE | 2.0 | 9.8 | 19.3/12.1 | 2.4/3.6 | 166.0 | 2130 | 18.7 | 47.6 | 77.4 | 74.3 | 79/76 | 3.8/3.8 |
| ACT | | Spunbond PET/PE | 3.2 | 14.5 | 40.2/23.5 | 3.7/3.0 | 71.2 | 2159.7 | 15.0 | 32.4 | 59.5 | 53.8 | 70/76 | 3.4/3.8 |
| Sontara | 8001 | Spunlace PET | 1.0 | 6.2 | 10.3/4.2 | 1.4/1.5 | 470.8 | 2103 | 24.0 | 61.6 | 152.3 | 46.7 | 78/42 | 3.8/3.8 |
| Sontara | 8004 | Spunlace PET | 1.6 | 8.2 | 22.2/3.8 | 1.5/2.5 | 249.3 | 2115.6 | 18.9 | 42.5 | 89.1 | 58.2 | 73/34 | 3.8/3.8 |
| Sontara | 8005 | Spunlace PET | 1.9 | 9.7 | 29.6/9.2 | 1.6/2.6 | 213.8 | 2104 | 16.7 | 42.3 | 79.8 | 61.1 | 82/46 | 3.8/3.8 |
| Sontara | 9008 | Spunlace PET | 2.0 | 10.1 | 21.5/8.2 | 1.5/2.2 | 208.2 | 2094.7 | 16.5 | 42.4 | 77.4 | 58.7 | 84/80 | 3.2/3.8 |
| Typar F | 5417-HS | Spunbond PP | 3.8 | 12.8 | 55.0/34.2 | 2.6/3.2 | 47.5 | 1791 | 12.3 | 39.7 | 158.5 | 57.6 | 54/56 | 0.9/1.4 |
| Delpore | 80 micron | PE Film-spot slit | 1.3 | 6.5 | 4.8/4.8 | .05/.07 | 45.5 | 1941.2 | 43.0 | 106.1 | 499.0 | 41.7 | 38/39 | 0.7/0.7 |
| Snofil | 40 micron | PET card/resin | 0.7 | 3.2 | 7.0/0.95 | 0.2/0.3 | 676.7 | 1899.1 | 36.3 | 98.4 | 422.6 | 33.2 | 74/73 | 2.1/2.3 |

Other materials, of course, could be used and are available from different vendors or manufacturers. For example, other candidate materials include the following commercially available products from Saatitech, Inc. (Somers, N.Y. USA):

Saatifil Nylon PA 64/47 (average pore size (in μm)/% effective open area)

Saatifil Nylon PA 70/49

Saatifil Nylon PA 55/43

Saatifil PES 53/40

Note: PA=Polyamide, PES=polyester. Numbers after each product indicate pore size and percent open area, respectively. Specific physical properties are publicly available.

Other possible materials are:

a. SNS, 1 micron, three layer composite (available from DuPont).

b. Film, Delnet—80 micron (Delstar Technologies, Inc., Austin, Tex. USA)

b. mean or average pore size (generally in the 50-80 micron range, and preferably less than 70 microns for wovens (it also appears better that the distribution in pore size be rather narrow—e.g. maximum/minimum=2×); for non-wovens the small average pore size may produce a better barrier to pollen because of the tendency for there to be tortuous paths through the material, which tends to trap particles that can enter it (conversely, larger average pore size for non-wovens may work as well as smaller average pore size for wovens for that same reason);

c. air/water permeability;

d. light transmissivity;

e. tensile strength and resistance to tear.

Table A indicates examples of materials having properties to consider for sock 10 or cover 20. If the primary function of the sock or shroud is blockage of pollen, primary material characteristics and properties would include sufficiently small pore size but maximum air and water permeability and maximum light transmissivity. In such situations, pore size and other factors would be selected to block most, if not all, of the relevant pollen but not be so small to materially effect fluid (gas and liquid) permeability or light transmissivity. The aim would be to be exclusionary to pollen, yet permeable to essential things needed for normal growth of the plant. Stated differently, the material would be a barrier or filter to pollen but the plant would grow essentially as if nothing was covering it (e.g. it would have a substantially similar growing environment as if outside the cover). The plant essentially would "think" it was outside, but pollen would be blocked. As can be appreciated, the pore size distribution needed for an application can be refined through testing. For example, materials of different properties, including different pore sizes and permeability, could be tested over a growing season by leaving a sock over the female parts of an entire plant. If no seeds are produced, the material can be considered to have effectively excluded all viable pollen.

Through empirical testing, pore size can be selected. For example, a candidate material could be placed around one or more plants during an entire growing season. If no seeds are produced by cross pollination, empirically it can be assumed the material blocks, or at least materially blocks, the relevant pollen. Monitoring of plant growth versus environmental conditions (relative to a control plant closely situated but not shrouded with the material) can empirically establish whether a material adversely effects growth of a plant. Temperature can be monitored to determine whether a material causes undesirable build-up of heat, which could affect the health of the plant or cause drying of the plant to a level which is undesirable. Presently, it is believed that a good performance level for excluding foreign pollen would be contamination by foreign pollen that does not exceed normal contamination of hand-pollinated kernels (approximately 2%).

Field purity testing of the plant sock on maize has shown the effectiveness of the pollen barrier. Although some contamination is inevitable in field conditions, such as pollen being carried by small insects crawling up inside the plant sock and transmitting pollen to the corn silks, results have demonstrated the pollen barrier provided by the fabrics is adequate for our needs.

Likewise, the plant sock also showed good performance in yield trials. Maize plants covered with the plant sock were effective at self pollination. The numbers of good kernels forming on each ear were adequate for our needs, and in some cases as high or higher than those from traditionally hand-pollinated plants. The plant sock already demonstrated effectiveness at blocking undesirable pollen in field purity testing, so with the yield trials performance, we have confidence that these kernels will have the desired genetic identity.

It should be understood, however, that pollen size can vary from type of plant to type of plant. Even for the same type of plant, pollen has size variability. It can also shrink in size as it dries, and remains viable while drying. The general rule of the invention would be, in use of the invention in plant pollination processes, to select a pore size that stops viable pollen.

It is also believed that to maximize air flow, pore size should be maximized and area of the material between pores minimized. Therefore the competing interests of blocking relevant pollen versus maximum permeability must be balanced. One way to increase permeability is to reduce the amount of material between pores. This increases the overall ratio of open area to material, which is believed to be better for increased air flow. It also tends to reduce the cost of the material, as less material is used per square inch of material. A balance between acceptable level of pollen filtration and air and water permeability is the goal. Pollen filtration is for "relevant" pollen for the particular plant, in the sense that the primary concern is to filter out pollen that would cause fertilization of the plant at issue. Thickness and weight might preferably be minimized in certain situations, especially where increased light transmissivity is desired or needed.

Additional options and alternatives for the invention include the following. Non-oven materials of average pore size even greater than average diameter of relevant pollen might possibly be used if they present a tortuous path between opposite sides of the material. For example, non-woven material with a tortuous path between sides tends to stop particles not only greater than the average pore size (e.g. 10 micron average pore size stops 0.3 micron particle) but a fraction of the size thereof. Generally, the smaller the pore size, the more expensive the material. Therefore, this might allow reduction of cost while maintaining an effective barrier against viable relevant pollen. Apertured films and other materials having the types of needed characteristics and properties might be used.

There may be situations where maximum light transmissivity is intentionally limited to specific wavelengths to influence plant growth (quality). There is usually a balance between small enough pore size for pollen exclusion but allowing enough light. There is many times a balance between light quality and light quantity. One example indicated as possibly advantageous in certain circumstances would be a material that transmits at least 5,000 foot-candles of light in the blue and red regions of the light spectrum (e.g. 400 to 700 nm wavelengths). In very hot or direct sunlight conditions, the material might be colored or coated in a manner to present either a heat absorbing or heat reflecting function. Again, such an addition might intentionally be used and be beneficial to growth of the plant in certain situations. It might be desirable to diffuse light and the material could be made to do so (e.g. neutral gray color could simulate some shade). There could be sprays, dyes, or coatings (e.g. aluminized) to filter certain light wavelengths but allow others.

A jig or tool could be used to assist in placing a plant sock 10 over a plant and then either be removed or left in place to function as a sock framework. The jig could have a framework to hold sock 10 in an expanded state to assist in slipping sock 10 over a plant. It could also be left in place to hold sock 10 away from the plant. It could also be used for smaller, weaker plants that cannot support sock 10.

One example of a jig is a 10 by 14 inch felt sheet with two wood dowels attached or sewn into the sheet along the short sides. A hook and loop fastener (e.g. Velcro®) could be attached to one short side. The jig could be used in the following procedure for deploying a sock 10 onto a growing corn plant prior to silk emergence. The felt sheet could be wrapped around the top part of the plant (including tassel) and secured by connecting the free end of the hook and loop fastener to the felt material to gently compress and reduce the diameter of the top of the plant. Care should be taken to use clean hands and to avoid disturbing or breaking the tassel or leaves. Sock 10 is rolled up (like a condom) and then its bottom opening placed over the top of the plant and the wrapped jig. Sock 10 is then gently unrolled (like a condom) down over the plant a ways. The worker can reach up, gently release the hook and loop fastener on the jig, and remove the jig through the bottom opening in sock 10. Sock 10 is then positioned relative to the plant so that the bottom is below the reproductive parts of the plant (e.g. two leaves below the ear) and preferably not too low (all the way down to the ground). Care should be taken to ensure there is sufficient excess space at the top of sock (e.g. 8 to 10 inches) to allow for vertical plant growth (this extra length would drape or hang ready to accept plant growth. The bottom of sock 10 would be cinched around the plant stem and secured (e.g. drawstring tied in slip knot).

Also, covering material might be used as a barrier against pollen moving out (pollen escape) from a plant inside the cover or shroud rather than against pollen coming in. One example would be with genetically modified organism (GMO) crops. Regulations tend to proscribe contamination of non-GMO crops by GMO crops. Thus, a plant sock 10, or perhaps better a shroud or tent 20, would of course be effective at blocking pollen from GMO plants inside the sock or tent escaping and thus risking contamination of non-GMO crops (by wind or insects carrying it). Presently, regulations tend to require GMO crops to be placed in fields that are separated by a certain distance (can be many yards) from non-GMO crops. This distance can be substantial. This can require additional land, which is expensive, and many times difficult to justify. Utilization of a tent or shroud 20 could provide sufficient assurance that no GMO pollen would escape to allow the GMO crops to be placed much closer (and even directly adjacent) to non-GMO crops (which could allow active use of more land and/or be less expensive).

It is believed possible to coat, impregnate, or otherwise impart chemicals to the material of the plant sock, shroud or tent. Examples could be pesticides. Such could assist in deterring the passage or even presence of these potentially detrimental things. The substances could be sprayed, brushed, or otherwise placed on the material. This could be repeated at time intervals, or different substances applied concurrently or sequentially.

As can be appreciated, the invention can be used for both inclusion and exclusion. It could keep pollen away for a plant or collection of plants. It could keep pollen in for a plant or collection of plants. It could be used to preserve a genotype.

The invention might also be used for the purposes of maintaining the purity of specially engineered plants producing what are sometimes called such as "nutraceuticals" or plants grown in what is sometimes called "pharming" or "biopharming". In such instances, plants may be genetically engineered to produce substances that are pharmaceutically active. Humans can then receive the pharmaceutically active substance or nutraceuticals by ingesting a pertinent part of the plant. It may be important to isolate such plants.

As stated, the invention is believed applicable at least to other plants (e.g. rye and other grasses, sorghum, wheat, and other wind pollinated small grains) and plant breeding. For example, it might be advantageous for small or weak plants (e.g. plants that cannot be hooped).

It would be desirable if the material could be washable and reusable.

Still additional options or alternatives for the invention are as follows.

Sock 10 could be tapered or have a larger cross-sectional area when expanded at one end or the other. For example, a narrow cross-sectional end could be easier to bind around the base of the plant, use less material, and have more expansion room for leaves and other growth above the base. Sock 10 could generally follow the shape of the plant, preferably with room for the plant to grow.

A draw string could be sewn in or otherwise installed at or near the opening to the sock for easier and more efficient installation. Another alternative could be an elastic band or material which could be sewn or installed in the sock around or near the opening.

Another option would be use of two different materials or a hybrid type of material made from more than one fabric. For example, some portion of the top of the plant sock or pollination cage could be shaded (like a hat or beret) to reduce incident light as a means to keep temperatures down (e.g. neutral gray to shade the top of the plant), while the remaining material down the sides would be of lower opacity and possibly higher air permeability. Colors could be used to reduce heat. Less heat might be generated inside sock 10 by using certain colors for all or part of the sock or tent. While it might reduce some amount of useful light for the plant(s), it can be selected and configured to allow sufficient light. Conversely, color or other modification of the fabric might be possible to increase heat inside the sock or tent, if needed (e.g. colder climates).

Another option might be dual texture surface on the material. For example, the inside of the sock could have a surface texture very smooth to facilitate placement/removal operations, as cottony material tends to catch and pull on plant foliage. A rougher outer surface could discourage insects and increase barrier properties to airborne contaminants.

Another option could include coating the fabric with Teflon® or other substances. For example, Teflon® could reduce friction or abrasion with the plant when the sock is placed over the plant, to help it slip over the plant. There could be one or more additional layers over the base or substrate material for a variety of functions.

Thus it can be seen that the invention can take many forms and embodiments.

In one aspect, a sock supported by the plant is placed over a substantial part of a whole growing plant. It is made of a material that has good air/water exchange and allows enough light to not substantially change the plant's normal growing environment, but blocks pollen or insects or other undesirables.

In another aspect, a plant or plural plants are tented or covered by a similar material. While the plant(s) might support the material, it could be supported by an independent frame or structure.

Another aspect involves covering plural plants but also covering individual plants or parts thereof under the larger cover.

Another aspect of the invention is selection of and a material itself which accomplishes desired goals.

Another aspect is use of a barrier to isolate a plant or plants, such as GMO plants, nutraceuticals, or pharming.

Another aspect of the invention is a method of increasing the window of time for completing pollination by using plant socks or tents.

Another aspect of the invention is use of a sock or tent to selectively control environmental factors to control growth or development of the plant. Further, a material with less than desired breathability might be useable if also made to transmit less light so that less heat is built up inside. Both air and humidity can be controlled.

As can be appreciated, air permeability, blockage of pollen of the relevant size, and opacity to light are taken into consideration. Other factors can be also. It is generally desirable to maximize air permeability, maximize blockage of pollen, and maximize light transmittance. However, sometimes a balance must be made between these sometimes competing factors.

What is claimed:

1. An apparatus for control of relevant pollen to or from a growing maize plant which includes a top and reproductive parts separated from each other below the top of the plant, without material damage to the plant or material inhibition, disruption, or affect on normal plant health or growth, comprising:
   a. a covering having a top, an elongated intermediate portion, and an open bottom and sized for placement over the plant top and down around a substantial amount of a plant, the substantial amount of the plant comprising at least the plant top, the separated reproductive parts and the plant therebetween, wherein the cover is tapered from a narrower top to a wider bottom for installation on a single plant;
b. a releasable closure adapted to close and cinch the open bottom around the plant so that the covering forms an enclosure around the substantial amount of the plant;
c. the covering comprising a flexible material which has:
  i. relatively high permeability to gas and moisture to allow effective transport of gas and water to and from the plant, the relatively high permeability comprising a Frazier value of approximately 650-1000 ft$^3$/ft$^2$/min. or higher;
  ii. pores of relatively small size comprising a very high frequency adapted to effectively block relevant viable pollen from passage to or from the plant by having a mean pore size smaller than normal sizes of relevant viable pollen, the pore size comprising between approximately 70/49 and 53/40 average pore size (in μm) to % effective open area;
  iii. substantial light transmissivity to allow effective passage of light to the plant, the substantial light transmissivity comprising a PAR transmission % for 400-700 nm light of at least 75%;
  iv. relatively light weight to allow draping of the material on the plant, the relatively light weight comprising approximately one oz/yd$^2$ or less so that support other than the plant is not required;
  v. resistance to deformation, tearing, and puncture during normal handling and moderate to high wind for the growing environment, wherein the resistance to deformation, tearing, and puncture comprises a tensile MD/XD of 10.3/42 lb/in, and a tear MD/XD of 1.4/1.5 lb. or better;
  vi. relatively high percent open area, the relatively high percent open area comprising an approximate range of 40%-50% so that the covering is a barrier to relevant pollen but is not a barrier to plant growth requisites;
  vii. relatively small thickness comprising an approximate range of 2.0-15 mils; and
  viii. relatively high moisture vapor transfer ratio in the range of approximately 1500-2500 g/100 m$^2$/day.

2. The apparatus of claim 1 wherein the single plant is a corn plant and the cover is approximately 60" tall, 9" across at top closed end, and 28-32" across at bottom open end, adapted to be secured above the ground and have some room for plant growth.

3. The apparatus of claim 1 wherein the cover is configured to cover a plurality of plants.

4. The apparatus of claim 3 further comprising a frame to suspend at least part of the cover over the plants.

5. The apparatus of claim 4 wherein the open bottom is positioned at or near the ground.

6. The apparatus of claim 1 wherein the gas comprises $O_2$, $CO_2$, and $H_2O$.

7. The apparatus of claim 1 wherein the moisture is in liquid form.

8. The apparatus of claim 1 wherein the relatively small pore size comprises a narrow distribution of mean pore size.

9. The apparatus of claim 1 wherein the material blocks relevant pollen and is breathable even in wet environments.

10. The apparatus of claim 1 wherein the relevant pollen is wind borne pollen for that type of plant.

11. The apparatus of claim 1 wherein the material is a fabric.

12. The apparatus of claim 11 wherein the material is made of nano-fibers.

13. The apparatus of claim 1 wherein the material has a relatively low co-efficient of friction.

14. The apparatus of claim 13 wherein the co-efficient of friction is between approximately 0.6/0.8 to 3.8/3.8 MD/CD and 38/39 to 84/80 slip angle.

15. The apparatus of claim 1 wherein the material is woven.

16. The apparatus of claim 1 wherein the material is non-woven.

17. The apparatus of claim 1 wherein the material is an apertured film.

18. The apparatus of claim 1 wherein the material presents a tortuous path to pollen.

19. The apparatus of claim 1 wherein the material is washable and reusable.

20. The apparatus of claim 1 wherein the ratio between maximum and minimum average pore size is on the order of two or less.

21. The apparatus of claim 1 further comprising a chemical impregnated in the material, the chemical selected from the set comprising herbicide, insecticide, and fungicide.

22. The apparatus of claim 1 wherein the pore size is effective to block all external pollen.

23. The apparatus of claim 1 herein the average pore size is smaller than 75 microns.

24. The apparatus of claim 1 wherein the average pore size is between 60 and 70 microns.

25. The apparatus of claim 1 wherein the weight of the material is less than one ounce per square yard.

26. The apparatus of claim 1 wherein the material is adapted to cover substantially all reproductive parts of a plant.

27. The apparatus of claim 1 wherein the material is adapted to cover a plurality of plants.

28. The apparatus of claim 1 wherein the material comprises first and second materials of different properties.

29. The apparatus of claim 28 wherein the two different materials can be used to selectively apply shade, heat regulation, or varying textures to the plant.

30. The apparatus of claim 1 wherein the material has areas of different textures.

31. The apparatus of claim 1 wherein the reproductive portions comprise two reproductive portions.

32. The apparatus of claim 1 wherein the reproductive portion comprise a male portion and a female portion.

33. The apparatus of claim 1 wherein the reproductive portions comprise three or more reproductive portions.

34. The apparatus of claim 1 wherein the plant comprises a corn plant.

* * * * *